United States Patent [19]

Kuyama et al.

[11] 4,075,326
[45] Feb. 21, 1978

[54] FUNGICIDAL/ALGICIDAL COMPOSITION FOR NON-MEDICAL USES

[75] Inventors: Hiroshi Kuyama, Urawa; Nobuyuki Higosaki, Tanashi, both of Japan

[73] Assignee: Rohm and Haas Company, Philadelphia, Pa.

[21] Appl. No.: 667,813

[22] Filed: Mar. 19, 1976

Related U.S. Application Data

[62] Division of Ser. No. 534,519, Dec. 19, 1974, Pat. No. 3,961,933.

[30] Foreign Application Priority Data

Dec. 22, 1973  Japan .................................. 49-3172

[51] Int. Cl.² ...................... A01N 11/02; A01N 11/04
[52] U.S. Cl. ........................................ 424/141; 71/67; 71/84
[58] Field of Search ................ 71/67, 97, 84; 424/141

[56] References Cited

U.S. PATENT DOCUMENTS 3,634,061   1/1972   Geiger et al. ............................ 71/67

FOREIGN PATENT DOCUMENTS

| 7,231,606 | 1972 | Japan | 71/67 |
| 7,242,483 | 1972 | Japan | 71/67 |
| 7,114,280 | 4/1971 | Japan | 424/141 |
| 829,479 | 3/1960 | United Kingdom | 424/141 |

*Primary Examiner*—Glennon H. Hollrah
*Attorney, Agent, or Firm*—George W. F. Simmons

[57] ABSTRACT

Fungicidal or algicidal agents are provided which consist of a copper salt of an acid which is an unsaturated dibasic acid of the formula

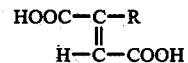

wherein R is hydrogen or lower alkyl together with an inorganic copper compound which is sparingly soluble or insoluble in water for example basic copper chloride, basic copper sulfate, basic copper carbonate, copper silicate, cuprous oxide, basic copper phosphate and copper hydroxide. The copper salt and the inorganic copper compound are preferably divided a finely as possible and thereafter mixed. The compositions are of low toxicity, provide a lasting effect and do not give rise generally to secondary noxious products.

4 Claims, No Drawings

FUNGICIDAL/ALGICIDAL COMPOSITION FOR NON-MEDICAL USES

This is a division of application Ser. No. 534,519 filed Dec. 19, 1974 now U.S. Pat. No. 3,961,933 granted June 8, 1976.

This invention relates to a novel non-medical fungicidal/algicidal agent which is little toxic to the human system and various economic organisms, provides a lasting effect, gives a decomposition product of low toxicity after serving its purpose, permits ready commercial production, gives rise to no noxious second product during its production and finds utility for a wide range of applications.

The agent of this invention is characterized by containing therein at least one member selected from each of the groups (A) and (B) given below. As occasion demands, it may additionally contain a component which belongs to neither of the groups.

A. copper salt of an unsaturated dibasic acid of the generic formula:

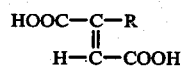

(wherein, R is a hydrogen atom or a lower alkyl group), copper terephthalate and copper isophthalate, and B. inorganic copper compounds sparingly soluble or insoluble in water, represented by basic copper chloride, basic copper sulfate, basic copper carbonate, copper silicate, cuprous oxide, basic copper phosphate and copper hydroxide.

The copper compounds belonging to groups (A) and (B) and used as essential components for the agent of this invention are desired to be divided as finely as practicable and the two components are also desired to be uniformly mixed. If the agent is used as an agronomical preparation to be applied to plants, it is desired to exclude water-soluble copper ions as far as permissible. This is because the agent has its functioning surface area increased and its effect manifested more easily in proportion as its particle size is reduced. Presence of a water-soluble copper ion is undesirable because it often bends to injure sensitive plants.

The compounds of the groups A and B of which the agent of this invention is composed are invariably stable and weakly reactive chemically and also stable physically. So, they are compatible with almost any other components. It can freely be admixed with other principal components as well as such adjuvants as carrier, stabilizer, surfactant, extender and toxicity-alleviator. In any event, the present invention is characterized by the state in which at least one component selected from the group A and at least one component from the group B coexist. The agent, of course, may be composed of two or more components selected from each of the groups.

In their admixed state, the compounds of the groups A and B seldom undergo decomposition or are rendered ineffectual under natural conditions.

The compounds of the groups will now be described specifically herein below and the characteristics of the agent of this invention in its formulated condition will be explained.

In the generic formula:

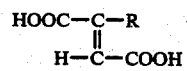

(wherein, R denotes a hydrogen atom or a lower alkyl) if R is a hydrogen atom, then the compound is fumaric acid having a chemical structure of:

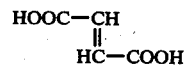

If R is a methyl group ($CH_3$—), then the compound is mesaconic acid having a chemical structure of:

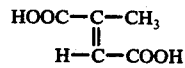

When such a dibasic carboxylic acid forms a copper salt, since copper is divalent, the resultant salt tends to assume the form of a high molecular compound or polymolecular compound. One example of the salt is this:

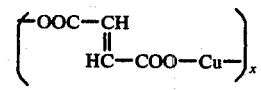

(wherein, $x$ is a positive integer)

The copper salt of a carboxylic acid thus has rather a highly stabilized bond reflecting a coordination bonding property than a mere ionic salt bond.

The toxicity of fumaric acid to the human system is extremely low. According to the "Report of Special Toxicity Study on 1000 Principal Chemical Products," (Japanese Edition, p. 181, published May 1, 1973 by Overseas Technical Data Reserch Institute) based on the results of the survey conducted by Arthur D. Little Inc. at the request of Environment Protection Bureau of the U.S. Government for example, it is given that "fumaric acid has weak pungence but very little toxicity to man." In the entry of "fumaric acid" in page 474 of "Merck Index" (8th Edition), a comprehensive chemical dictionary published by Merck, possession of extremely low toxicity is indicated and possibility of this acid taking place of tartaric acid for use in refreshing beverage and baking powder is also described.

Terephthalic acid and isophthalic acid are aromatic dicarboxylic acids having the following structures respectively:

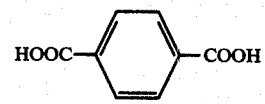

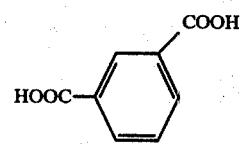

They serve as components of the polyesters which are produced and used in large quantities as one form of raw materials for synthetic resin and synthetic fiber. They are produced commercial on a large scale. Particularly as synthetic fiber, polyesters are used in large quantities for clothing and underwears.

Particularly, an elaborate study has been given to the toxicity of terephthalic acid. For example, the acute toxicity, $LD_{50}$, of the acid to mice is 5000 mg/kg or over in the case of oral administration and 1430 mg/kg in the case of intraabdominal administration. The acute toxicity, $LD_{50}$, of disodium terephthalate is 6300 mg/kg in oral administration and 4600 mg/kg in intra-abdominal administration. It has been demonstrated by the in-vivo metabolism test using rats that terephthalic acid which enters the rats' systems is wholly excreted quantitatively out of the system and that no part of the acid remains to be accumulated within the system. The test for chromic toxicity has also been conducted on mice. Feed containing 0.5% of terephthalic acid given them over a long period of time has not been recognized to produce any toxic effect. Administration of terephthalic acid has no effect whatever on the liver and the kidneys. Since terephthalic acid accelerates absorption of tetracycline type antibiotics, additive use thereof in animal feed is authorized by the government in Japan. An experiment to ascertain safety of the prolonged use of this substance on mice, rabbits and chickens has been continued by keeping two generations of the animals under observation. It has been demonstrated that the substance is excreted from the animals' organs without delay and that there is absolutely no possibility of the substance remaining in eggs, chicken and pork. Absence of toxicity in terephthalic acid is substantiated by the observation that addition of 0.3% of terephthalic acid to feed has an effect of accelerating the growth of chickens and shoats. Thus, it may safely be concluded that terephthalic acid or a salt thereof which possibly occurs in consequence of the decomposition of copper salt of terephthalic acid, a principal component of the agent of this invention, is substantially innoxious.

When terephthalic acid or isophthalic acid, particularly the former, forms a salt with divalent copper, it is more like to produce a high molecular copper salt between terephthalic acid molecules than to form a salt within the molecules. Consequently, the resultant salt assumes a structure having terephthalic acid groups linked with a copper atom interposed therebetween, as illustrated by the formula:

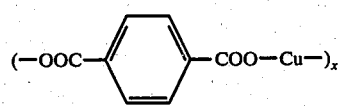

(x = positive integer)

The properties of this compound as a polymer are introduced in the "Chemical Abstracts," Vol. 57, page 2397 (1962). The copper salt of a carboxylic acid is not a mere salt-bond compound but rather seems to be a compound possessed of an extremely strong bond reflecting coordinate bonding property. In this connection, the aforementioned literature uses an expression "Co-ordination polymer" to suggest the structure. This compound, therefore, has a structure characterized by having the copper ion quite stably and strongly retained within the high molecular unit.

The fact that the organic copper compounds belonging to the group A find utility in non-medical fungicidal/algicidal preparations has already been found by the same inventors.

Said utility is disclosed in detail in Japanese Patents No. 690,265 and No. 680,947 (Patent Publication No. 42483/72 and Patent Publication No. 31606/72). The disclosures may be summarized as follows:

1. Since the copper ion which has high fungicidal/algicidal capacity is retained in a stabilized state, the activity is manifested for a long period of time.
2. There is no possibility of the copper ion being released all at once in a large amount so as to do harm to the object intended to be given required protective treatment.
3. The compound is wholly a stable high molecular substance and possesses covering and protecting capacity.
4. The compound is chemically stable so as to withstand admixture of any other components.

The chemical structures of the compounds in question are described in detail in the specifications of the patent publications made in the name of the same inventors.

Now a description will be made of inorganic copper salts sparingly soluble or insoluble in water belonging to the Group B. As fungicides, these compounds of the group B have been used longer than any other compounds. These copper type fungicides utilize the fungicidal property of copper ion. Since the copper ion can do harm to economic crops and other useful organisms, the compounds are prepared in a form sparingly soluble or totally insoluble in water so that the copper ion may be released with graduality enough to keep from producing any toxic effect. The oldest of all the copper compounds is Bordeaux liquid which was discovered in 1885 in France. This compound is still serving as one of the most important fungicide for use in agriculture. The Bordeaux liquid is prepared by spot formulation using copper sulfate and lime prior to use; the preparation is therefore highly complicated and time-consuming. It has a disadvantage that its physical properties and effects are affected by the conditions of preparation. In view of the difficulties, there has been devised a method whereby sparingly soluble or insoluble copper salts are formulated in the form of wettable powder or dust so that they may be directly put to use. The copper compounds formulated in this manner include basic copper chloride (copper oxychloride) basic copper sulfate, basic copper carbonate, copper silicate, cuprous oxide, basic copper phosphate, basic copper sulfophosphate and copper hydroxide. They are specific examples of the members of the group B.

Copper, particularly copper ion, when admitted in a large quantity into the human system or useful organisms, has a toxic effect: Plants are particularly susceptible to the injuries done thereby. Copper is widely distributed naturally in organic systems, though in a smaller amount than iron. It is not noxious when it is absorbed or taken in piecemeal in small amounts. It is also contained in soil to a fairly high level of concentrations. Since it is a metal with which man has kept contact from the distant past, he is well versed in the mechanism of its toxic effect, the method for eliminating the toxic effect, the method for avoiding the poison, etc. In this respect, copper compounds are far easy to handle and control than organic compounds which are newly synthesized and have room for doubt as to physiological activities such as those associable with deformation and cancerous growth. This may possibly explain why the Bordeaux liquid still occupies the position of the most important agricultural fungicide in spite of the fact that millions of organic substances have already been synthesized and a great many fungicidal organic synthetic compounds have been brought to public knowledge. The outstanding attributes of copper compounds as fungicides are that, if they are used so as not to produce any toxic effects, they exhibit protective fungicidal activities not inferior to those of any other newly developed organic synthetic fungicides and that their effects are brought upon a wide spectrum of pathogenic microorganisms. Frequently organic compounds of complicaated structures are effective on a narrow spectrum of microorganisms (fungi, bacteria and their respective subdivision members) (that is to say, having a narrow fungicidal spectrum). It is often noted that they exhibit good fungicidal effects on specific microorganisms and have virtually no effect on other microorganisms.

The inorganic copper salts belonging to the group B are, as explained above, sparingly soluble or totally insoluble and seem to be gradually decomposed inwardly from the surface to release copper ion and manifest the expected effect. Therefore, such physical propeties as grain size have particularly important bearing upon the effect thus manifested. There are indications that the readiness with which the effect is brought out increases with the increasing fineness of the salts. The particle size distribution is also one factor for the effect manifestation.

The compounds of the groups A and B for use as essential components of the agent of this invention have been described. The agent of this invention is characterized by simultaneously containing at least one member each of the aforementiond groups A and B. If occasion demands, it may contain other effective component than those of the groups A and B or adjuvants other than effective components.

It has been found that when the components selected from the two groups are admixed, the effects of the individual components as actually manifested are greatly improved so much as to render the agent highly feasible. Possession of fungicidal/algicidal activity by the compounds of the group A has been reported in detail in the aforementiond offical gazette of patent publication by the same inventors. The practical utility of the compounds of group B has long been known to the art.

The reason for the unexpectedly great enhancement in the actual effect derived from the admixture of the high molecular copper salts of the group A and the sparingly soluble or totally insoluble inorganic copper compounds of the group B is unknown at this stage. The fact that the admixture increases the lasting property of the protective fungicidal power and the fact that the total copper content is increased because the inorganic copper compounds of the group B generally have large copper contents than the high molecular copper salts belonging to the group A undoubtedly have some bearing upon the enhanced effect. Another possible reason is that the condition, speed, timing, etc. of the gradual release of copper ion by the organic copper compounds of the group A are different from those of the inorganic coppers belonging to the group B and the exquisite combination of differences existing therebetween functions synergistically to enhnace the fungicidal effect.

These are invariably conjectures. The fact is that the admixed components manifest a conspicuous cooperative action and bring about a recognized improvement in the effect. This improved effect particularly stands out when the agent is used as a fungicide for agronomical applications. The admixture of the components from the groups A and B gives birth to a novel agent which shows high practical utility in constant conformity to the combination of various factors such as locality, species of crop, kind of pest, condition of cultivation.

Now, preparation of the compounds of the group A, preparation of the compounds of the group B, admixture of the components selected and related matters will be described specifically with reference to working examples.

Terephthalic acid, isophthalic acid or fumaric acid is dissolved in the aqueous solution of a caustic alkali or ammonium hydroxide to form an aqueous solution of water-soluble salt such as alkali salt or ammonium salt. This solution is brought into contact with the aqueous solution of such water-soluble copper salt as copper sulfate, copper nitrate or copper chloride. Immediately, the copper salt of carboxylic acid precipitates in most cases in the form of a sparingly soluble or totally insoluble multimolecular copper salt. The contact may be effected by adding the copper salt to the aqueous solution of alkali salt of acid, adding the latter to the former or adding the two at the same time. Particularly when this product is intended as a spray for agronomical use, it is desirable that the formed salt is washed so as to be deprived of as much water-soluble copper ion as possible. The organic copper salt thus prepared is dried and pulverized. Although the degree of pulverization differs with the purpose of use, the copper salt generally is more effective in a finely divided form. For use as a spray for agronomical use, the grain size is desired to be smaller than 300 – 320 mesh. The effect is conspicuous when the average grain size is in the range of from several microns to 1 micron. The procedure of manufacture just described is intended to serve as an illustration and has no bearing whatever upon the scope of the present invention.

The inorganic copper salts belonging to the group B are sparingly soluble or practically insoluble solids. They are driable and pulverizable. In a dried, pulverized form they are available on the market. The organic copper salt from the group A and the inorganic copper compound from the group B are mixed. Otherwise they are mixed and subsequently pulverized. These are the most ordinary practices observed. Optionally, various other effective components and adjuvants may be incorporated into the resultant mixture.

The organic acid copper salts of the group A are not limited to only simple copper salts exclusively of phthalic acid, isophthalic acid and fumaric acid. Substances in which they are contained as principal organic acid components will suffice for the purpose. Other polybasic acids may partially be used to take place of these dibasic acids. It is also permissible to use other monofunctional acids such as, for example, benzoic acid, salicylic acid, halogenobenzoic acid and halogenosalicyclic acid partially in conjunction therewith in producing copper salts mentioned above. For example, a copper salt of the type described above produced by using the dibasic carboxylic acid incorporating a small quantity of tricarboxylic acid functions as a cross-linking agent in the formation of a high molecular compound and represents a useful embodiment of this invention. Other kinds of metals may partially be contained to form a part of the copper salt bond. Examples of the metal advantageous for this purpose are manganese, nickel, iron, zinc etc.

EXAMPLE 1

Terephthalic acid (I), isophthalic acid (II), fumaric acid (III) and mesaconic acid (IV) as a polybasic organic acid were tested. The various copper salts described herein below were prepared. Copper terephthalate was dried and finely divided by a micronizer to an average particle diameter (as determined by Fischer Sub-sieve sizer -F.S.S.S.) of 1,2 μ (I-1).

Terephthalic acid incorporating therein 5 mol% of benzoic acid was converted into a mixed sodium salt and further into a copper salt. The resultant copper salt was similarly dried, finely divided to an average particle diameter of 1.1 μ (I-2).

Terephthalic acid incorporating therein 5 mol% of benzene1,3,5-tricarboxylic acid was converted into a mixed sodium salt in the form of aqueous solution and further into a copper salt. The resultant copper salt was similarly dried and finely divided to an average particle diameter of 1.2 μ (I3).

The aqueous solution of sodium terephthalate was combined with copper sulfate and zinc sulfate to cause coprecipitation. In this case, the molar ratio of Cu : Zn 95 : 5 was used. The resultant copper salt was dried and finely divided to an average particle diameter of 1.3 μ (I4).

Copper isophthalate was dried and finely divided to an average particle diameter of 1.5 μ (II-1).

In all the copper salts described above, the copper contents were 21 – 24% as copper equivalent.

Copper fumarate was dried and finely divided to an average particle diameter of 1.2 μ (III-1).

Fumaric acid incorporating therein 5 mol% of terephthalic acid was converted into a mixed sodium salt in the form of aqueous solution and double decomposed with a copper salt. The resultant copper salt was dried and finely divided to an average particle diameter of 1.4 μ (III-2).

Fumaric acid incorporating therein 5 mol% of benzene-1,3,5-tricarboxylic acid was converted into a mixed sodium salt in the form of aqueous solution and then double decomposed with a water-soluble copper salt. The resultant copper salt was dried and finely divided to an average particle diameter of 1.5 μ (III-3).

Copper mesaconate was dried and finely divided to an average particle diameter of 1.4 μ (IV-1).

The samples of (III-1) throgh (IV-11) were found to have copper contents of the order of 30 to 33 %.

As inorganic copper salts of the group B, those described below were used.

Basic copper chloride (copper oxychloride) (Bayer: "Cupravit Forte" ), copper content 41% (B-1)
Basic copper sulfate (Tomono Noyaku), copper content 32% (B-2)
Basic copper phosphosulfate (Takeda), copper content 23% (B-3)
Cupric hydroxide (Sankyo), copper content 54% (B-4)
Copper silicate, copper content 21% (B-5)
Powdered copper cuprous oxide, copper content 70% (B-6)

Those copper salts which had already been formulated for use as agricultural pesticides were dried and finely divided to particle diameters fine enough to pass 325 mesh. They are also incorporated by extenders. Those which had not been formulated for use as agricultural pesticides were dried, crushed and further divided finely to particle diameters such that 95% or more of the powders passed 325 mesh.

The finely divided organic copper salts belonging to the group A and the finely divided inorganic coppers belonging to the group B were combined in varying weight ratios, mixed as uniformly as permissible by using an ordinary mixing machine such as a ribbon mixer. During the mixing, sodium lignosulfonate, potassium lignosulfonate and other extenders were incorporated. The resultant mixtures were again mixed and finely divided through a micronizer. The final test samples thus produced were found to have average particle diameters of the order of 1.0 to 1.5 μ (F.S.S.S.). Of the individual compounds of the groups A and B, those which had already been formulated as agricultural pesticides were put to use in their unmodified form and those which had not been formulated as agricultural pesticides were combined uniformly with extenders and finely divided again through a micronizer to average particle diameters of the order of 1.0 – 1.5 μ (F.S.S.S.), respectively prior to test. All the samples formulated as agricultural pesticides were invariably in the form of wettable powder. In most comparative tests, they were suspended in water and tested for behaviors of wettable powders. Some of the samples were prepared in the form of dust and applied by means of a duster to be tested for pest control. Comparision of their effects revealed no significant difference ascribable to the particular types of agents.

EXAMPLE 2

Wettable powders of the following formulations were used.

a. A wettable powder composed of 50 parts by weight of (I-1) and 50 parts by weight of (B-1).
b. A wettable powder composed of 90 parts by weight of (I-1) and 10 parts by weight of (B-1).
c. A wettable powder composed of 30 parts by weight of (I-1) and 70 parts by weight of (B-1).
d. A wettable powder composed of 10 parts by weight of (I-1) and 90 parts by weight of (B-1).
e. A wettable powder composed of 50 parts by weight of (I-1) and 50 parts by weight of (B-2).
f. A wettable powder composed of 50 parts by weight of (I-1) and 50 parts by weight of (B-3).
g. A wettable powder composed of 50 parts by weight of (I-1) and 50 parts by weight of (B-4).
h. A wettable powder composed of 50 parts by weight of (I-1) and 50 parts by weight of (B-5).
i. A wettable powder composed of 80 parts by weight of (I-1) and 20 parts by weight of (B-6).
j. A wettable powder composed of 50 parts by weight of (II-1) and 50 parts by weight of (B-1).
k. A wettable powder composed of 50 parts by weight of (II-1) and 50 parts by weight of (B-4).
l. A wettable powder composed of 50 parts by weight of (III-1) and 50 parts by weight of (B-1).
m. A wettable powder composed of 80 parts by weight of (III-1) and 20 parts by weight of (B-4).
n. A wettable powder composed of 20 parts by weight of (III-1) and 80 parts by weight of (B-4).
o. A wettable powder composed of 50 parts by weight of (IV-1) and 50 parts by weight of (B-1).
p. A wettable powder composed of 30 parts by weight of (I-1), 30 parts by weight of (III-1) and 40 parts by weight of (B-1).
q. A wettable powder composed of 40 parts by weight of (I-1), 20 parts by weight of (B-1) and 40 parts by weight of (B-4).

EXAMPLE 3

Tests were performed as to the control of downy mildew *Pseudoperonospore cubensis* attacking cucumbers. The disease appeared in the middle part of June and exuberated in the latter part of July. Application was made on July 3, 13, 20 and 27, at the dosage rate of 2 liters each in the former two applications and 3 liters each in the latter two applications respectively by spraying by use of a small powered sprayer. On Aug. 7 (11 days after the last application), 50 leaves from 7 stocks per plot were visually examined to find disease leaf ratio, disease spot distribution per unit area and phytotoxicity.

Preparations used for the test:

| |
|---|
| Wettable powder of basic copper chloride having copper content of 47% (B-1), (Bayer, "Cupravit Forte"), 500 dilutions |
| Wettable powder of copper terephthalate (T Company), 500 dilutions |
| Wettable powder of (a) of Example 2, 500 dilutions |
| Wettable powder of (b) of Example 2, 500 dilutions |
| Wettable powder of (c) of Example 2, 500 dilutions |
| Wettable powder of (d) of Example 2, 500 dilutions |
| Wettable powder of (e) of Example 2, 500 dilutions |

Results of test:

| Preparation used | Disease ratio (%) | Disease spot distribution (%) | Rating of Phytotoxicity |
|---|---|---|---|
| B-1 | 39.5 | 20.4 | + + |
| B-2 | 43.6 | 27.2 | + + |
| I-1 | 36.5 | 26.1 | — |
| a | 12.7 | 8.6 | — |
| b | 13.4 | 7.9 | — |
| c | 15.4 | 8.2 | — |
| d | 17.6 | 9.2 | — |
| e | 16.5 | 7.8 | — |
| No treatment | 99.0 | 87.0 | — |

EXAMPLE 4

Tests were performed as to the control of anthracnose *colletotrichum lagenariuem* attacking water-melons under normal field conditions. The disease occurred in the first part of July and grew rapidly thereafter. In the middle part of July, the disease was accompanied by a complication. The water melons put to test were of the species "Akebono". One plot was 20 m² in area. Application was made with a small powered sprayer on May 31, June 6, June 13, June 20, June 28, July 4, July 11 and July 18, at a dosage rate of 200 liters per 10 area on and before June 20 and 300 liters per 10 are thereafter. On July 20, the plants were visually examined for disease leaf ratio and disease fruit ratio. On July 27, they were examined for disease fruit ratio.

The preparations used were the solutions, each of 500 dilutions, of the following:

| | | |
|---|---|---|
| B-1 | (l) | (I-4) |
| B-2 | (o) | (II-1) |
| B-3 | (p) | (III-1) |
| B-5 | (q) | (III-2) |
| (f) | (I-1) | (III-3) |
| (h) | (I-2) | (IV-1) |
| (j) | (I-3) | |

| Preparation used | Disease leaf ratio (%) | Disease fruit ratio (July 20) (%) | Disease fruit ratio (July 27) (%) | Phytotoxicity |
|---|---|---|---|---|
| B-1 | 45.6 | 26.5 | 52.5 | + + |
| B-2 | 47.5 | 31.5 | 54.5 | + + |
| B-3 | 46.5 | 29.5 | 50.5 | + + |
| B-5 | 46.5 | 30.5 | 56.5 | + + |
| (f) | 26.5 | 12.5 | 26.5 | — ~ + |
| (h) | 24.5 | 11.6 | 27.5 | — ~ + |
| (j) | 19.5 | 10.7 | 30.6 | — ~ + |
| (l) | 20.5 | 11.5 | 24.5 | — ~ + |
| (o) | 24.5 | 11.6 | 25.5 | — ~ + |
| (p) | 18.5 | 10.5 | 26.5 | — ~ + |
| (q) | 17.5 | 12.5 | 25.5 | — ~ + |
| (I-1) | 35.8 | 19.5 | 36.2 | — ~ + |
| (I-2) | 34.5 | 28.6 | 32.5 | — ~ + |
| (I-3) | 35.5 | 27.5 | 34.6 | + |
| (I-4) | 36.5 | 19.5 | 34.5 | — ~ + |
| (II-1) | 40.5 | 24.6 | 46.5 | — ~ + |
| (III-1) | 35.6 | 22.7 | 45.5 | + |
| (III-2) | 34.5 | 24.5 | 46.5 | + |
| (III-3) | 35.6 | 23.5 | 46.5 | — ~ + |
| (IV-1) | 34.5 | 29.5 | 46.5 | + |
| No treatment | 99.2 | 57.5 | 88.0 | — |

EXAMPLE 5

Tests were performed as to the control of bacterial canker (*xanthomonas vesicatoria*) attacking tomatos under selected field conditions favoring the occurrence of the disease. First sign of the disease of bacterial canker was seen in the middle part of July. A fair degree of disease contraction was observed in the plots of no treatment. In all plots including even no-treatment plots, late blight and leaf-mild were not observed to occur to any appreciable extent. On July 1, 7, 15, 21 and 28 and Aug. 5, 22 and 30, the diluted preparations were sprayed at a fixed dosage rate of 200 liters/10 ares. On Aug. 22, the plants were examined for disease condition Preparations used:

| | | |
|---|---|---|
| B-4 | 1000 | dilutions |
| Maneb Dithane | 600 | " |
| (g) | 1000 | " |
| (k) | " | " |
| (m) | " | " |
| (n) | " | " |
| (q) | " | " |
| (I-1) | " | " |
| (II-1) | " | " |
| (III-1) | " | " |

Effect of Bacterial Spot Control

| Preparation used | Degree of disease (%) | Phytotoxicity |
|---|---|---|
| B-4 | 4.5 | — ~ + |
| I-1 | 6.5 | — |
| II-1 | 8.5 | — |

| | -continued | |
|---|---|---|
| B-4 | 1000 | dilutions |
| Maneb Dithane | 600 | " |
| (g) | 1000 | " |
| (k) | " | " |
| (m) | " | " |
| (n) | " | " |
| (q) | " | " |
| (I-1) | " | " |
| (II-1) | " | " |
| (III-1) | " | " |

Effect of Bacterial Spot Control

| Preparation used | Degree of disease (%) | Phytotoxicity |
|---|---|---|
| III-1 | 9.5 | − ~ + |
| Maneb Dithane (600 dilutions) | 14.5 | — |
| (g) | 1.5 | — |
| (k) | 2.5 | — |
| (m) | 1.9 | — |
| (n) | 1.4 | — |
| (q) | 0.9 | — |
| No application | 25.8 | — |

EXAMPLE 6

Tests were performed as to the control of various diseases attacking citrus. As concerns melanose (*Diaporthe citri*), spray of 500 dilutions of (a), (b); (c) (d) and (e) on pots, nursery beds and fields containing citrus trees provided a control of disease by 65 – 70%. By contrast, the 500 dilutions of the uncombined components (I-1), (B-1) and (B-2) provided a control of 50% (I-1) and 30% (B-1) and (B-2) respectively and invariably produced a toxic effect on citrus trees. As regards canker (*Xanthomonas citri*), 500 dilutions of (a), (b), (c) and (i) were tested in conjunction with 500 dilutions of (I-1) and (B-1) and commercially available Streptomycin preparation. Those of (I-1) and (B-1) provided a control inferior to that of Streptomycin preparation, whole those of (a), (b), (c) and (i) gave a control not inferior to that of Streptomycin preparation.

EXAMPLE 7

Various finely divided compounds were dispersed in aqueous emulsion paint bases and spread on nylon ropes and allowed to dry. The ropes were held immersed in fresh water for two months under natural conditions. The nylon rope which had not been painted was found to be covered throughout with alga. Organic copper salts used along gave inferior control of alga. Inorganic copper salts gave practically perfect control for the first one to two weeks but, thereafter, suffered rapid algal growth throughout the rope surface. The ropes coated with the preparations according to the present invention suffered the least surface contamination by algal growth. These preparations showed the control for a prolonged period.

We claim:

1. A fungicidal composition which comprises a fungicide which consists essentially of a combined effective amount of at least one compound selected from Group A and at least one compound selected from Group B wherein Group A is a copper salt of an unsaturated dibasic acid of the formula:

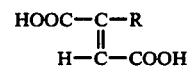

wherein R is a hydrogen atom or a lower alkyl group and Group B is an inorganic copper salt selected from the group consisting of copper oxychloride, basic copper sulfate, basic copper carbonate, copper silicate, cuprous oxide, basic copper phosphate and copper hydroxide, the ratio of A to B being from 1:9 to 9:1.

2. A fungicidal composition according to claim 1 wherein R is hydrogen or methyl.

3. A fungicidal composition according to clalim 1 wherein the copper salt of the unsatuated dibasic acid is copper fumarate and the inorganic copper salt is copper oxychloride.

4. A fungicidal composition according to claim 1 wherein the copper salt of the unsaturated dibasic acid is copper mesaconate and the inorganic copper salt is copper oxychloride.

* * * * *